United States Patent
Gigler et al.

(10) Patent No.: US 9,822,059 B2
(45) Date of Patent: Nov. 21, 2017

(54) METHOD FOR SEPARATING HIGH-BOILING CARBOXYLIC ACID VINYL ESTER/CARBOXYLIC ACID MIXTURES

(71) Applicant: Wacker Chemie AG, München (DE)

(72) Inventors: Peter Gigler, Dachau (DE); Jürgen Stohrer, Pullach (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 15/315,162

(22) PCT Filed: May 21, 2015

(86) PCT No.: PCT/EP2015/061231
§ 371 (c)(1),
(2) Date: Nov. 30, 2016

(87) PCT Pub. No.: WO2015/185365
PCT Pub. Date: Dec. 10, 2015

(65) Prior Publication Data
US 2017/0113998 A1 Apr. 27, 2017

(30) Foreign Application Priority Data

Jun. 6, 2014 (DE) .................. 10 2014 210 835

(51) Int. Cl.
| | |
|---|---|
| C07C 67/54 | (2006.01) |
| C07C 51/573 | (2006.01) |
| C07C 51/56 | (2006.01) |
| B01D 3/00 | (2006.01) |
| C07C 7/148 | (2006.01) |
| C07C 51/54 | (2006.01) |

(52) U.S. Cl.
CPC .............. *C07C 67/54* (2013.01); *B01D 3/009* (2013.01); *C07C 51/56* (2013.01); *C07C 51/573* (2013.01); *C07C 7/148* (2013.01); *C07C 7/14875* (2013.01); *C07C 51/54* (2013.01)

(58) Field of Classification Search
CPC ....... C07C 51/54; C07C 51/56; C07C 51/573; C07C 67/10; C07C 67/54; C07C 7/148; C07C 7/14875; B01D 3/009
See application file for complete search history.

(56) References Cited

U.S. PATENT DOCUMENTS

| | | | |
|---|---|---|---|
| 2,997,494 A | 8/1961 | Brown | |
| 2,997,495 A | 8/1961 | Rutledge et al. | |
| 3,000,918 A | 9/1961 | Rubenstein et al. | |
| 3,117,145 A * | 1/1964 | Ehrreich | C07C 69/01 530/215 |
| 3,158,633 A | 11/1964 | Monroe, Jr. et al. | |
| 3,179,641 A | 4/1965 | Brown et al. | |
| 3,188,319 A * | 6/1965 | Jurgen Smidt et al. | C07C 67/10 548/479 |
| 3,201,357 A | 8/1965 | IFairman et al. | |
| 3,736,236 A * | 5/1973 | Lucio di Fiore et al. | C07C 7/08 203/51 |
| 4,425,277 A | 1/1984 | Kawamoto et al. | |
| 4,981,973 A | 1/1991 | Murray | |
| 5,214,172 A | 5/1993 | Waller | |
| 5,821,384 A * | 10/1998 | Zoeller | C07C 67/00 560/231 |
| 2014/0343310 A1 | 11/2014 | Geisel et al. | |

FOREIGN PATENT DOCUMENTS

| | | |
|---|---|---|
| DE | 102013224491 A1 | 6/2015 |
| DE | 102013224496 A1 | 6/2015 |
| DE | 102014206915 A1 | 10/2015 |
| DE | 102014206916 A1 | 10/2015 |
| GB | 827718 | 2/1960 |
| GB | 869830 | 6/1961 |
| GB | 869828 | 6/1969 |
| JP | 5279296 A | 10/1993 |
| JP | 07138203 A | 5/1995 |
| WO | 9209554 A1 | 6/1992 |
| WO | 2011139360 A1 | 11/2011 |
| WO | 2011139361 A1 | 11/2011 |
| WO | 2013117294 A1 | 8/2013 |

OTHER PUBLICATIONS

International Search Report and Written Opinion for International Application PCT/EP2015/061231, dated Aug. 27, 2015, 8 pages.

* cited by examiner

*Primary Examiner* — Yate K Cutliff

(74) *Attorney, Agent, or Firm* — RatnerPrestia

(57) ABSTRACT

The invention relates to a method for separating a mixture containing at least one carboxylic acid vinyl ester of general formula R'—C(O)O—CH=CH$_2$ and at least one carboxylic acid of general formula R'—COOH, wherein R' in either case can be an aliphatic group having 12 to 22 C atoms or a cycloaliphatic group having 12 to 22 C atoms, or an aromatic group having 12 to 22 C atoms, and R' can be identical or different, characterized in that the carboxylic acid is converted to its anhydride R'—C(O)—O—C(O)—R' and the carboxylic acid vinyl ester is subsequently separated.

11 Claims, No Drawings

METHOD FOR SEPARATING HIGH-BOILING CARBOXYLIC ACID VINYL ESTER/CARBOXYLIC ACID MIXTURES

CROSS-REFERENCE TO RELATED APPLICATIONS

This application is a U.S. National Phase Application of PCT International Application PCT/EP2015/061231, filed May 21, 2015, claiming priority benefit of German Application DE 10 2014 210 835.7, filed Jun. 6, 2016, the disclosures of which are incorporated herein in their entirety.

BACKGROUND

The invention relates to a process for separating high-boiling vinyl carboxylate ester/carboxylic acid mixtures.

The distillative separation of mixtures of high-boiling vinyl carboxylate esters and high-boiling carboxylic acids becomes increasingly difficult with increasing molecular weight of the components. The terms high-boiling vinyl carboxylate esters and high-boiling carboxylic acids are to be understood as meaning vinyl carboxylate esters and carboxylic acids each having at least 12 carbon atoms in the carboxylic acid radical. The reason for the difficult fractionation thereof are boiling points that are very high and close together. This becomes clear for example from the boiling points of vinyl palmitate (346° C. at 1 bar abs.) and palmitic acid (351° C. at 1 bar abs.) or vinyl stearate (385° C. at 1 bar abs.) and stearic acid (361° C. at 1 bar abs.). A distillative fractionation of such components having boiling points that are very high and close together is not possible on a large-industrial scale, particularly when carboxylic acids/vinyl carboxylate esters of different chain lengths are present in the mixture.

Such mixtures of vinyl carboxylate esters and carboxylic acids are generated for example in the transvinylation of carboxylic acids when the reactant carboxylic acid has at least 12 carbon atoms. Transvinylation is the transfer of a vinyl unit from a reactant vinyl ester (1V) to a reactant carboxylic acid (2S) to generate a product vinyl ester (2V) and the corresponding acid of the reactant vinyl ester (1S).

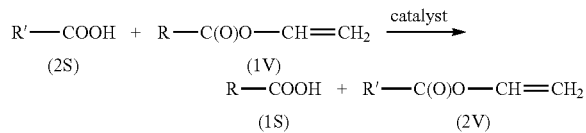

Distillative removal of low-boiling components (usually the reactant vinyl ester, for example vinyl acetate, and the corresponding acid thereof, for example acetic acid) affords the mixture of vinyl carboxylate ester and carboxylic acid to be separated.

The production of high-boiling vinyl carboxylate esters by means of transvinylation is described in the examples of numerous patent publications. Pd-catalyzed transvinylations for preparing vinyl palmitate and vinyl stearate are described in WO 2011/139360 A1 (examples 69 and 70), JP 05-279296 A (example 1) and U.S. Pat. No. 5,214,172 A (examples 19-40 and 56-57) while the Hg-catalyzed variant finds application in U.S. Pat. No. 3,158,633 A (examples 1-5), GB 827718 A (example 15). WO 2011/13936C A1 does not elaborate on the workup of the product mixture. JP 05-279296 also provides no indications in this regard. U.S. Pat. No. 5,214,172 A is concerned with the activity of Pd catalysts in transvinylation without addressing the workup of the product mixture. U.S. Pat. No. 3,158,633 A does not elaborate on the workup of the reaction product either. GB 827718 mentions that the product vinylester may be distilled off without describing specific measures.

The removal of vinyl stearate by fractional distillation is referred to in JP 07-138203 A (example 8), U.S. Pat. No. 4,425,277 A (example 24) and U.S. Pat. No. 3,188,319 A (example 2). A precise configuration of this separation process and likewise a chemical analysis of the distillation fractions are not described. Only example 2 of U.S. Pat. No. 3,188,319 A reports a boiling point of the product, namely 203° C. at 5 mmHg (~376° C. at 1 bar). It stands to reason that in these cases a mixture of stearic acid and vinyl stearate was removed since stearic acid (361° C. at 1 bar) has a lower boiling point than the corresponding vinyl stearate (385° C. at 1 bar).

U.S. Pat. No. 3,000,918 A claims a process for separating vinyl carboxylate ester/carboxylic acid mixtures where, by addition of sodium hydroxide, the carboxylic acid is converted into the corresponding low-volatile Na salt which may be removed from the vinyl carboxylate ester by filtration. Said ester may then be purified by distillation. The same process is utilized in U.S. Pat. No. 3,179,641 A for preparing vinyl phenylstearate. As described in example 1 after removal of vinyl acetate and acetic acid the remaining phenylstearic acid is converted into the low-volatile Na salt by addition of sodium hydroxide and the vinyl ester is removed by distillation. The removal of the Na salt necessitates a solid-liquid separation step which entails a great deal of process engineering complexity and represents a disadvantage of this process. While the Na salt may be reused after conversion back into the carboxylic acid, this also requires an additional chemical process step. Both specifications further describe that decomposition reactions and polymerization of the vinyl ester occur during the distillation if the reactant carboxylic acid is not removed beforehand.

GB 869830 A discloses a process for producing vinyl stearate where vinyl stearate is removed from stearic acid by extraction with an aliphatic hydrocarbon. This may optionally be followed by a further purification through various adsorbents. The authors describe that when commercial stearic acid is employed this process is applicable only up to a palmitic acid proportion of 30% since the extraction becomes more difficult with an increasing proportion of palmitic acid. Vinyl carboxylate ester/carboxylic acid mixtures based on commercial stearic acid 50 which has a palmitic acid proportion of up to 50 wt % accordingly cannot be separated with this process. This extraction process is also described in the specifications: U.S. Pat. No. 2,997,494 A (example 1), U.S. Pat. No. 2,997,495 A (example 7), GB 869828 A (example 1) and U.S. Pat. No. 3,201,357 A (example 12).

SUMMARY

High-boiling vinyl carboxylate esters can no longer be separated from the corresponding carboxylic acids by distillation. This is relevant especially for the products from transvinylation reactions which are based on high-boiling carboxylic acids, for example the commercially available mixtures of palmitic and stearic acid. In addition to an extraction method for vinyl stearate produced from stearic acid in >70 wt % purity the prior art describes the reactive conversion of the carboxylic acid into corresponding low-volatile Na carboxylates. However, these require a complex solid-liquid separation step and also an additional chemical process step to convert the Na carboxylate back into the carboxylic acid. A broadly applicable process for separating high-boiling vinyl carboxylate ester/carboxylic acid mixtures which forgoes complex process steps for solids removal and conversion back into the carboxylic acid is hitherto unknown.

The problem addressed by the present invention was therefore that of developing a process for separating high-boiling vinyl carboxylate ester/carboxylic acid mixtures which is notable for broad applicability to high-boiling vinyl carboxylate esters/carboxylic acids or corresponding mixtures and also requires no complex solid-liquid separation step.

The invention provides a process for separating a mixture comprising at least one vinyl carboxylate ester of general formula R'—C(O)O—CH=CH$_2$ and at least one carboxylic acid of general formula R'—COOH, wherein in each case R' may be an aliphatic radical having 12 to 22 carbon atoms or a cycloaliphatic radical having 12 to 22 carbon atoms or an aromatic radical having 12 to 22 carbon atoms and R' may be identical or different, characterized in that the carboxylic acid is converted into its anhydride R'—C(O)—O—(O)—R' and the vinyl carboxylate ester is subsequently removed.

The process allows vinyl carboxylate esters of general formula R'—C(O)O—CH=CH$_2$, wherein R' is an aliphatic radical having 12 to 22 carbon atoms or a cycloaliphatic radical having 12 to 22 carbon atoms or an aromatic radical having 12 to 22 carbon atoms, to be removed from one mixture. Vinyl carboxylate esters having different radicals R' may also be present in the mixture. Examples include vinyl esters of lauric acid, myristic acid, palmitic acid, stearic acid, naphtalenecarboxylic acid or mixtures thereof. Particular preference is given to using vinyl esters of carboxylic acids having 15 to 22 carbon atoms, such as palmitic acid and stearic acid and mixtures thereof.

DETAILED DESCRIPTION

Carboxylic acids which may be present in the mixture with the vinyl carboxylate ester are carboxylic acids of general formula R'—COOH, wherein R' may be an aliphatic radical having 12 to 22 carbon atoms or a cycloaliphatic radical having 12 to 22 carbon atoms or an aromatic radical having 12 to 22 carbon atoms. Carboxylic acids with different radicals R' may also be present in the mixture. Examples thereof include lauric acid, myristic acid, palmitic acid, stearic acid, naphtalenecarboxylic acid or mixtures thereof. Particular preference is given to fatty acids having 15 to 22 carbon atoms, such as palmitic acid and stearic acid and mixtures thereof.

The mixture of carboxylic acid R'—COOH and vinyl carboxylate ester R'—C(O)O—CH=CH$_2$ may comprise further components, for example from a transvinylation reaction, such as catalysts, anhydrides, acids and polymeric constituents.

The molar fraction x of the carboxylic acid R'—COOH relative to the mixture of vinyl carboxylate ester R'—C(O)O—CH=CH$_2$ and carboxylic acid R'—COOH may be 0 mol %<x<100%, preference being given to a proportion of 0.01 mol %≤x≤50 mol %, particular preference being given to a ratio of 0.1 mol %≤x≤30 mol %.

In a first preferred embodiment the conversion of the carboxylic acid R'—COOH into the corresponding anhydride R'—C(O)—O—C(O)—R' is effected by reaction with an anhydride of general formula R*—C(O)—O—C(O)—R*, wherein R* is identical or different and represents an aliphatic radical having 1 to 10 carbon atoms or a cycloaliphatic radical having up to 10 carbon atoms or an aromatic radical having up to 10 carbon atoms. Examples thereof include the anhydrides of the acids: acetic acid, propionic acid, n-butyric acid, isobutyric acid, n-valeric acid, 2-methylbutyric acid, 3-methylbutyric acid, pivalic acid, caproic acid, cyclohexanecarboxylic acid, n-heptanoic acid, 2-methylhexanoic acid, 2-ethylhexanoic acid, n-octanoic acid, n-nonanoic acid, isononanoic acid, neononanoic acid, n-decanoic acid, neodecanoic acid. Preference is given to employing the anhydride of acetic acid (acetic anhydride).

0.1 to 5 molar equivalents of the anhydride R*—C(O)—O—C(O)—R* relative to the carboxylic acid R'—COOH are employed. It is preferable when 0.25 to 3 molar equivalents of the anhydride are employed, particularly preferably 0.5 to 2 molar equivalents, in each case relative to the carboxylic acid R'—COOH.

The reaction of the mixture comprising a vinyl carboxylate ester R'—C(O)O—CH=CH$_2$ and a carboxylic acid R'—COOH with the anhydride R*—C(O)—O—C(O)—R* is generally effected at temperatures of 0° C. to 150° C., preferably at 30° C. to 120° C., particularly preferably at 50° C. to 100° C. The reaction time is generally up to 5 hours, preferably up to 2 hours, particularly preferably 5 to 60 minutes. The pressure at which the reaction is effected is generally 0.001 to 10 bar abs., preferably 0.1 to 2 bar, particular preference being given to operation at standard pressure (1 bar abs.).

In a second preferred embodiment the conversion of the carboxylic acid R'—COOH into its anhydride R'—C(O)—O—C(O)—R' may be effected by transition-metal-catalyzed reactive distillation with a vinyl carboxylate ester of general formula R—C(O)O—CH=CH$_2$, wherein R may be an aliphatic radical having 1 to 10 carbon atoms or a cycloaliphatic radical having up to 10 carbon atoms or an aromatic radical having up to 10 carbon atoms. Preference is given to using low molecular weight vinyl carboxylate esters, wherein R is an alkyl radical having 1 to 6 carbon atoms. Particular preference is given to using vinyl acetate.

Preferred catalysts are Ru compounds or Pd compounds typically employed for transvinylation reactions. Suitable catalysts are known to a person skilled in the art, for example from WO 2011/139360 A1, WO 2011/139361 A1 and U.S. Pat. No. 4,981,973, the disclosure of which in this regard is hereby incorporated by reference. Preference is given to employing Ru compounds. Particular preference is given to using Ru acetate or an active Ru catalyst solution of the type known to a person skilled in the art from laid-open patent applications DE 102014206915 and DE 102014206916.

The molar ratio of vinyl carboxylate ester R—C(O)O—CH=CH$_2$ to carboxylic acid R'—COOH may be 1:1 to 40:1.

Preference is given to a ratio of vinyl carboxylate ester to the carboxylic acid of 10:1 to 30:1, particular preference being given to a ratio of 15:1 to 25:1.

The reactive distillation is generally performed at a temperature of 100° C. to 180° C., preferably at a temperature of 120° C. to 160° C. The pressure at which the reactive distillation is effected is generally 1 bar abs. The reaction is preferably performed in a protective gas atmosphere, for example nitrogen, in a manner known per se.

The residence time in the reactor is generally 1 to 10 hours, preferably 3 to 8 hours.

The reactor employed may be a bubble column or a continuous stirred tank. Preference is given to employing a continuous stirred tank.

The reactive distillation to convert the carboxylic acid R'—COOH into the corresponding anhydride R'—C(O)—O—C(O)—R' may be performed separately or in combination with a transvinylation reaction implemented in the form of a reactive distillation. In this case once the transvinylation reaction has been effected the reactive distillation is continued, and the carboxylic acid R'—COOH thus converted into the corresponding anhydride R'—C(O)—O—C(O)—R', until the content of residual carboxylic acid R'—COOH in the reaction mixture is preferably not more than 5 wt %.

In both preferred embodiments conversion of the carboxylic acid R'—COOH into its anhydride R'—C(O)—O—C(O)—R' is followed by fractionation of the reaction mixture composed of vinyl carboxylate ester R'—C(O)O—CH=$CH_2$ and the anhydride R'—C(O)—O—C(O)—R'.

The mixture may optionally comprise further components such as catalysts, anhydrides, acids and polymeric constituents. The fractionation of the mixture is preferably effected by distillation. The pressure and temperature of the distillation and the configuration of the distillation columns depend on the components present in the product mixture and may be determined for example by means of routine tests performed by a person skilled in the art.

The process according to the invention for separating a mixture comprising at least one vinyl carboxylate ester of general formula R'—C(O)O—CH=$CH_2$ and at least one carboxylic acid of general formula R'—COOH may be performed following a transvinylation of a carboxylic acid of general formula R'—COOH with a vinyl ester of general formula R—C(O)O—CH=$CH_2$ and employed for fractionating the thus obtained reaction mixture. For example following a transvinylation of vinyl acetate with stearic acid and/or palmitic acid which is catalyzed with a ruthenium or palladium catalyst. The process conditions of a transvinylation are known to a person skilled in the art, for example from WO 92/09554 A1, WO 2011/139360 A1, WO 2011/139361 A1, WO 2013/117294 A1, WO 2013/117294 A1, DE 102013224491 and DE 102013224496, the disclosure of which in this regard is hereby incorporated by reference.

The process according to the invention makes it possible to separate any desired mixtures of high-boiling vinyl carboxylate esters and high-boiling carboxylic acids. Conversion of the high-boiling carboxylic acid into the corresponding higher boiling carboxylic anhydride allows the vinyl carboxylate ester to be removed.

It has been found that, surprisingly, the conversion of the high boiling carboxylic acid into the higher boiling carboxylic anhydride by reaction with a lower boiling anhydride can be achieved in simple fashion and with high selectivity.

Surprisingly, conversion of the carboxylic acid into the higher boiling carboxylic anhydride by reactive distillation with a lower boiling vinyl carboxylate ester in the presence of a catalyst is also successful. A solid-liquid separation step which entails a great deal of process engineering complexity is not required. When the fractionation of the high-boiling vinyl carboxylate ester/carboxylic acid mixtures is performed in combination with a transvinylation reaction the obtained anhydride R'—C(O)—O—C(O)—R' of the carboxylic acid R'—COOH can be directly reemployed in a transvinylation reaction without a further chemical process step being necessary beforehand.

The process according to the invention makes high-boiling vinyl carboxylate esters and any desired mixtures thereof easily obtainable on a large-industrial scale.

EXAMPLES

The examples which follow serve to more particularly elucidate the invention.

The reported compositions of the reaction mixtures were determined by means of quantitative NMR spectroscopy.

Example 1

Separation of a Vinyl Stearate/Stearic Acid Mixture by Addition of Acetic Anhydride A mixture of 35 g (113 mmol) of vinyl stearate (ABCR #AB123736) and 15 g (53 mmol) of stearic acid (Merck # 800673) was admixed with 8.1 g (79 mmol) of acetic anhydride (Aldrich # 110043) and stirred for 1 hour at 80° C. before excess acetic anhydride and the acetic acid formed were removed on a rotary evaporator. The mixture obtained thereafter was composed of 96.2 wt % vinyl stearate, 3.2 wt % stearic anhydride and 0.6 wt % stearic acid. Vacuum distillation at 100° C.-120° C. (0.02 mbar abs.) afforded the vinyl stearate in 99% purity.

The example shows that addition of acetic anhydride converts the stearic acid into stearic anhydride and that vinyl stearate can be obtained in high purity via a subsequent vacuum distillation.

Example 2

Separation of a Vinyl Stearate/Stearic Acid Mixture from a Transvinylation Reaction by Addition of Acetic Anhydride (in the Absence of Catalyst)

In a 100 ml Berghoff autoclave 20.0 g (70 mmol) of stearic acid (Merck # 800673), 48.4 g (562 mmol) of vinyl acetate (Wacker Chemie AG), 0.068 g (0.3 mmol) of phenothiazine and 0.086 g (0.3 mmol) of [$Ru_3O(OAc)_6$($H_2O$)$_3$]OAc (in the form of an acetic acid solution comprising 4.5 wt % Ru from Umicore) were heated to 140° C. for 4 hours at not more than 10.0 bar abs. Once cooled, acetic acid and vinyl acetate were removed on a rotary evaporator. Vinyl stearate and stearic acid were then distilled off at 154° C.-173° C. (1 mbar abs.).

The obtained 18.5 g of a mixture of 94 wt % (17.4 g, 56 mmol) vinyl stearate and 6 wt % (1.1 g, 4 mmol) stearic acid were admixed with 0.59 g (6 mmol) of acetic anhydride (Aldrich # 110043) and stirred for 1 hour at 80° C. before excess acetic anhydride and the acetic acid formed were removed on a rotary evaporator. Renewed vacuum distillation at 173° C. (1 mbar abs.) afforded the vinyl stearate in 99.8% purity.

Example 3

Separation of a Vinyl Stearate/Stearic Acid Mixture from a Transvinylation Reaction by Addition of Acetic Anhydride (in the Presence of Catalyst)

In a 100 ml Berghoff autoclave 20.0 g (70 mmol) of stearic acid (Merck # 800673), 48.4 g (562 mmol) of vinyl acetate (Wacker Chemie AG), 0.068 g (0.3 mmol) of phenothiazine and 0.086 g (0.3 mmol) of [$Ru_3O(OAc)_6$($H_2O$)$_3$]OAc (in the form of an acetic acid solution comprising 4.5 wt % Ru from Umicore) were heated to 140° C. for 4 hours at not more than 10.0 bar abs. Once cooled, acetic acid and vinyl acetate were removed on a rotary evaporator.

The reaction mixture which comprised 19.2 g (62 mmol) of vinyl stearate and 1.56 g (5.5 mmol) of stearic acid was then admixed with 1.12 g (11 mmol) of acetic anhydride (Aldrich # 110043) and stirred for 1 hour at 80° C. before excess acetic anhydride and the acetic acid formed were removed on a rotary evaporator. Vacuum distillation at 105° C.-130° C. (0.07 mbar abs.) afforded the vinyl stearate in 99% purity.

Example 4

Separation of a Vinyl Palmitate/Palmitic Acid Mixture from a Transvinylation Reaction by Reactive Distillation with Vinyl Acetate 220 g/h of a mixture of palmitic acid (Carl Roth #5907.2) and catalyst (active Ru catalyst solution based on $RuCl_3$, as disclosed in DE 102014206915, 1000 ppm Ru relative to palmitic acid) and 27.7 l/min of gaseous vinyl acetate were introduced into a 2 l glass reactor equipped with a dip tube. Vinyl acetate and the acetic acid formed were discharged in gaseous form and condensed outside the reactor. The reaction was performed with a constant reactor fill volume of 1750 ml, an average residence time of 6.7 hours and at an internal reactor temperature of 140° C. A mixture composed of 76 wt % vinyl palmitate, 20 wt % palmitic anhydride and 4 wt % palmitic acid was obtained. Removal of the vinyl palmitate was effected via a vacuum distillation at 150° C. (1 mbar abs.).

Example 5

Separation of a Vinyl Stearate/Stearic Acid Mixture from a Transvinylation Reaction by Reactive Distillation with Vinyl Acetate 225 g/h of a mixture of stearic acid (Carl Roth #9459.2) and catalyst (active Ru catalyst solution based on $RuCl_3$, as disclosed in DE 102014206915, 1000 ppm Ru relative to stearic acid) and 25.5 l/min of gaseous vinyl acetate were introduced into a 2 l glass reactor equipped with a dip tube. Vinyl acetate and the acetic acid formed were discharged in gaseous form and condensed outside the reactor. The reaction was performed with a constant reactor fill volume of 1750 ml, an average residence time of 6.5 hours and at an internal reactor temperature of 140° C. A mixture composed of 79 wt % vinyl stearate, 18 wt % stearic anhydride and 3 wt % stearic acid was obtained. Removal of the vinyl stearate was effected via a vacuum distillation at 175° C. (1 mbar abs.).

The invention claimed is:

1. A process for separating a mixture comprising at least one vinyl carboxylate ester of general formula R'—C(O)O—CH=$CH_2$ and at least one carboxylic acid of general formula R'—COOH, wherein in each case R' may be an aliphatic radical having 12 to 22 carbon atoms or a cycloaliphatic radical having 12 to 22 carbon atoms or an aromatic radical having 12 to 22 carbon atoms and R' may be identical or different, said process comprising the steps of converting the carboxylic acid into its anhydride R'—C(O)—O—C(O)—R' and subsequently removing the vinyl carboxylate ester.

2. The process as claimed in claim 1, wherein the conversion of the carboxylic acid R'—COOH into the corresponding anhydride R'—C(O)—O—C(O)—R' is effected by reaction with an anhydride of general formula R*—C(O)—O—C(O)—R*, wherein R* is identical or different and represents an aliphatic radical having 1 to 10 carbon atoms or a cycloaliphatic radical having up to 10 carbon atoms or an aromatic radical having up to 10 carbon atoms.

3. The process as claimed in claim 2, wherein 0.1 to 5 molar equivalents of the anhydride R*—C(O)—O—C(O)—R* relative to the carboxylic acid R'—COOH are employed and the reaction is effected at temperatures of 0° C. to 150° C., at a pressure of 0.001 to 10 bar abs., and with a reaction time of up to 5 hours.

4. The process as claimed in claim 2, wherein the anhydride of general formula R*—C(O)—O—C(O)—R* employed is an anhydride selected from the group consisting of anhydrides of acetic acid, propionic acid, n-butyric acid, isobutyric acid, n-valeric acid, 2-methylbutyric acid, 3-methylbutyric acid, pivalic acid, caproic acid, cyclohexanecarboxylic acid, n-heptanoic acid, 2-methylhexanoic acid, 2-ethylhexanoic acid, n-octanoic acid, n-nonanoic acid, isononanoic acid, neononanoic acid, n-decanoic acid, and neodecanoic acid.

5. The process as claimed in claim 1, wherein the conversion of the carboxylic acid R'—COOH into the corresponding anhydride R'—C(O)—O—C(O)—R' is effected by transition-metal-catalyzed reactive distillation with a vinyl carboxylate ester of general formula R—C(O)O—CH=$CH_2$, wherein R may be an aliphatic radical having 1 to 10 carbon atoms or a cycloaliphatic radical having up to 10 carbon atoms or an aromatic radical having up to 10 carbon atoms.

6. The process as claimed in claim 5, wherein the reactive distillation is performed in the presence of Ru compounds or Pd compounds as catalyst, with a molar ratio of vinyl carboxylate ester R—C(O)O—CH=$CH_2$ to carboxylic acid R'—COOH of 1:1 to 40:1 and at a temperature of 100° C. to 180° C.

7. The process as claimed in claim 5, wherein the vinyl carboxylate ester R—C(O)O—CH=$CH_2$ employed is a vinyl carboxylate ester having an alkyl radical having 1 to 6 carbon atoms as radical R.

8. The process as claimed in claim 1, wherein the vinyl carboxylate ester is removed by distillation.

9. The process as claimed in claim 1, wherein the conversion of the carboxylic acid into its anhydride is preceded by a transvinylation of a carboxylic acid of general formula R'—COOH with a vinyl carboxylate ester of general formula R—C(O)O—CH=$CH_2$.

10. The process as claimed in claim 9, wherein the transvinylation comprises a transvinylation of vinyl acetate with stearic acid and/or palmitic acid which is catalyzed with a ruthenium or palladium catalyst.

11. The process as claimed in claim 7, wherein the vinyl carboxylate ester is vinyl acetate.

* * * * *